(12) United States Patent
Merkel et al.

(10) Patent No.: US 9,469,594 B2
(45) Date of Patent: Oct. 18, 2016

(54) METHOD FOR STOPPING A REACTION DURING THE PRODUCTION OF AROMATIC AMINES FROM NITROAROMATICS

(71) Applicant: Bayer MaterialScience AG, Leverkusen (DE)

(72) Inventors: Michael Merkel, Dusseldorf (DE); Thomas Knauf, Dormagen (DE); Cliff Andre Peters, Schmedeswurth (DE); Thorsten Schmidt, Nindorf (DE); Karl-Heinz Wilke, Moers (DE)

(73) Assignee: Covestro Deutschland AG, Kaiser-Wilhelm-Allee, Leverkusen (DE)

( * ) Notice: Subject to any disclaimer, the term of this patent is extended or adjusted under 35 U.S.C. 154(b) by 0 days.

(21) Appl. No.: 14/394,142

(22) PCT Filed: Apr. 12, 2013

(86) PCT No.: PCT/EP2013/057716
§ 371 (c)(1),
(2) Date: Oct. 13, 2014

(87) PCT Pub. No.: WO2013/156409
PCT Pub. Date: Oct. 24, 2013

(65) Prior Publication Data
US 2015/0087862 A1    Mar. 26, 2015

(30) Foreign Application Priority Data

Apr. 16, 2012  (EP) .................................... 12164324

(51) Int. Cl.
C07C 209/36     (2006.01)
C07C 209/84     (2006.01)

(52) U.S. Cl.
CPC ........... *C07C 209/36* (2013.01); *C07C 209/84* (2013.01)

(58) Field of Classification Search
CPC .................................................... C07C 209/36
See application file for complete search history.

(56) References Cited

U.S. PATENT DOCUMENTS

| | | |
|---|---|---|
| 3,136,818 A | 6/1964 | Sperber et al. |
| 3,684,740 A | 8/1972 | Cimbalo et al. |
| 4,265,834 A | 5/1981 | Birkenstock et al. |
| 5,808,157 A | 9/1998 | Langer et al. |
| 5,877,350 A | 3/1999 | Langer et al. |
| 6,043,394 A | 3/2000 | Langer et al. |
| 8,044,244 B2 | 10/2011 | Seidemann et al. |
| 2008/0234518 A1 | 9/2008 | Sommer et al. |

FOREIGN PATENT DOCUMENTS

| | | |
|---|---|---|
| DE | 1133394 | 7/1962 |
| GB | 1452466 | 10/1976 |

*Primary Examiner* — Clinton Brooks
(74) *Attorney, Agent, or Firm* — N. Denise Brown

(57) ABSTRACT

The present invention relates to a method for producing aromatic amines by the hydrogenation of aromatic nitro compounds. This method supplies aromatic nitro compounds and hydrogen to a reactor and contacts them with a hydrogenation catalyst; and stops the supply of aromatic nitro compounds and hydrogen to the reactor. The supply of aromatic nitro compounds and hydrogen to the reactor is stopped to ensure safe shutdown of the reactor.

10 Claims, No Drawings

METHOD FOR STOPPING A REACTION DURING THE PRODUCTION OF AROMATIC AMINES FROM NITROAROMATICS

CROSS-REFERENCE TO RELATED APPLICATION

This application is a National Phase application to PCT/EP2013/057716, filed Apr. 12, 2013 and European Application No.: 12164324.1, filed Apr. 16, 2012.

FIELD OF THE INVENTION

The present invention relates to a process for preparing aromatic amines by hydrogenation of aromatic nitro compounds, which comprises the steps of introduction of aromatic nitro compounds and hydrogen into a reactor with contacting of a hydrogenation catalyst and of stopping the introduction of aromatic nitro compounds and hydrogen into the reactor.

BACKGROUND

Aromatic amines are important intermediates which have to be prepared inexpensively and in large amounts. For this reason, production plants for aromatic amines are generally built for very high capacities. The high productivity of these plants is ensured by means of very long reaction cycles and trouble-free running between the start-up and shutdown operations of the hydrogenation for regeneration of the hydrogenation catalysts used.

Aniline is an important intermediate, e.g. for the preparation of methylenedi(phenyl isocyanate) (MDI) and is generally produced on an industrial scale by catalytic hydrogenation of nitrobenzene by means of hydrogen. Particular preference is given to reaction conditions as described in GB 1 452 466 A1, EP 0 011 090 A1 or EP 0 944 578 A2 (isothermal mode of operation) and in EP 0 696 574 B1, EP 0 696 573 B1, EP 1 882 681 A1 (adiabatic mode of operation). Apart from the abovementioned processes using stationary catalyst beds, processes using fluidized catalyst beds have also been described, e.g. in DE 1114820 B, DE 1133394 B or WO 2008/034770 A1.

In all the adiabatic and isothermal processes described, the starting material nitrobenzene is reacted with an excess of hydrogen.

The preparation of the aromatic amines is carried out in reaction cycles because the catalyst activity of the hydrogenation catalysts decreases steadily.

The activity of used catalysts for the hydrogenation of aromatic nitro compounds therefore has to be restored at periodic intervals. For this purpose, a regeneration is carried out by removing carbon-containing deposits from the catalyst by burning-off in a stream of air. In other embodiments of the process, the burning-off step is followed by a washing step, e.g. as described in U.S. Pat. No. 3,684,740. The next reaction cycle can then be started, starting up the hydrogenation plant again.

EP 0 944 578 A2 (page 2, lines 1-20) discusses the start-up procedure for an adiabatic process for the hydrogenation of nitro compounds to form the corresponding amines. There, it is stated that increasing the space velocity of aromatic nitro compounds used over the catalyst continuously or stepwise to the maximum space velocity over a period of from 10 to 1000 hours has an advantageous effect on the space-time yield.

The quality of a process for the hydrogenation of aromatic nitro compounds is firstly defined by the content of undesirable hi-products of the reaction in the product. Secondly, the quality of a hydrogenation process is defined by the entire process of hydrogenation cycle, shutdown of the hydrogenation, regeneration of the hydrogenation catalyst and start-up of the hydrogenation process being able to be operated without a technical production stoppage.

In general, supported metal catalysts which have a preferred temperature window for optimal activity are used for heterogeneously catalyzed gas-phase processes. If the maximum temperature is exceeded only briefly, damage to the catalyst, e.g. as a result of sintering processes of the active metal particles on the support material, can occur.

Although the above-described processes of the prior art make it possible to prepare aromatic amines with high selectivity and in high yield, they describe, with the exception of EP 0 944 578 A2 which describes the start-up procedure, only processes which are already in operation and are running steadily. The possible problems in the start-up of a process for preparing aromatic amines are passed over.

SUMMARY

It was therefore an object of the present invention to provide a process which ensures trouble-free shutdown of the hydrogenation reaction and which does not lead to unsafe plant states or to damage to the hydrogenation catalyst so that breakthrough of the nitroaromatic to be hydrogenated through the catalyst bed occurs during start-up or after short hydrogenation cycles.

According to the invention, this object is achieved by a process for preparing aromatic amines by hydrogenation of aromatic nitro compounds, which comprises the steps:
A) introduction of aromatic nitro compounds and hydrogen into a reactor with contacting of a hydrogenation catalyst;
B) stopping of the introduction of aromatic nitro compounds and hydrogen into the reactor;
wherein step B) is carried out by
B1) firstly stopping the introduction of aromatic nitro compounds into the reactor so that aromatic nitro compounds remaining in the reactor and/or in plant parts fluidically connected upstream to the reactor react with the hydrogen which continues to be fed in and
B2) subsequently stopping the introduction of hydrogen after a predetermined time and/or after the concentration of aromatic nitro compounds in the gas stream entering the reactor goes below a predetermined value.

It has surprisingly been found that the object can be achieved for a hydrogenation process of aromatic nitro compounds when (expressed simply and without being restricted thereto) it is ensured during shutdown of the reaction that hydrogen is present in a sufficient amount in the reaction spaces until all nitroaromatics have reacted fully with hydrogen and have thus been consumed.

One of the advantages of this procedure is that carbon-containing organic compounds are largely removed from the reaction space through which the circulating gas flows and therefore can no longer interfere in the subsequent regeneration by consuming oxygen.

DETAILED DESCRIPTION

A reaction cycle is preferably shut down by firstly reducing the introduction of the starting materials (nitroaromatic and hydrogen) to a fraction of the nominal load. The introduction of nitrobenzene is then completely interrupted while maintaining all other operating parameters. The introduction of hydrogen is continued until the last residues of the nitroaromatic in the reaction spaces have been consumed.

Plant parts fluidically connected upstream to the reactor are, in particular, feed lines, collection vessels, flanges, vaporizers, heat exchangers, superheaters and the like in which residues of nitroaromatics can be present. On renewed start-up, these residues would be carried into the reactor.

When the reaction spaces and preferably also the periphery thereof are firstly freed of nitroaromatics before start-up of a reaction cycle, the following advantages are obtained:
  i) No excessive temperature on the catalyst which adversely affects the catalyst activity or reduces the productivity of the plant occurs.
  ii) The product quality does not suffer because of repeated start-up operations which are typically associated with a low initial selectivity until stable process conditions have become established.
  iii) Hydrogenation of nitrobenzene residues by means of a hydrogen excess which is too small, which leads to increased bi-product formation and carbonization of the catalyst, is avoided.
  iv) No safety problem occurs since no subatmospheric pressure arises in the plant. Dangers posed by a subatmospheric pressure are possible damage to plant parts which are not resistant to vacuum and that air intrudes into the plant and an explosive atmosphere can be formed. This has to be avoided at all costs in a hydrogenation plant.
  v) The energy costs for prolonged/more frequent regeneration and repeated start-up are saved.
  vi) Losses of aniline resulting from combustion during regeneration and longer downtimes for the regeneration which are associated therewith are largely avoided.

It is particularly advantageous for shutdown of the hydrogenation for the catalyst to contain catalytically active components on an aluminum oxide support having an average diameter of the aluminum oxide particles in the range from 1.0 mm to 7.0 mm and have a BET surface area of less than 20 $m^2/g$, and in which the active components comprise at least:
  (a) 1-100 g/l of support of at least one metal of groups 8 to 12 of the Periodic Table of the Elements, and
  (b) 0-100 g/l of support of at least one transition metal of groups 4 to 6 and 12 of the Periodic Table of the Elements, and also
  (c) 0-100 g/l of support of at least one metal of the main group elements of groups 14 and 15 of the Periodic Table of the Elements.

The groups of the Periodic Table of the Elements are in this text numbered in accordance with the IUPAC recommendation of 1986.

The aluminum oxide support preferably has an approximately spherical shape and preferably a diameter in the range from 1.0 mm to 7.0 mm.

Preferred reactors for an isothermally operated reactor are thermostatted tube reactors or shell-and-tube reactors. Suitable embodiments of such reactors are described, for example, in DE 2 201 528 A1, DE 2 207 166 A1, DE 198 06 810 A1, EP 1 439 901 A1, EP 1 569 745 A1, EP 1 590 076 A1, EP 1 587 612 A1, EP 1 586 370 A1, EP 1 627 678 A1 or DE 202 006 014 116 U1.

Preferred reactors for an adiabatically operated reactor are those described in DE 10 2006 035 203, paragraphs [0030] to [0033].

It is possible for the catalyst arranged in the reactor to be present in a filter candle through which radial flow occurs. This can be achieved, for example, by the catalyst being retained in a basket which is made up of two concentric, cylindrical mesh jackets having fluid-permeable walls. Here, one mesh jacket has a greater radius than the other, which is also referred to as central tube, and the space between the mesh jackets is the reaction space. A bottom of this hollow cylinder is preferably completely closed tight, while the other is closed only up to the central tube which is open at this end. The fluid can then flow in a radial direction from the outside inward and then be discharged through the central tube. As an alternative, the fluid can also be fed in through the central tube and then flow in a radial direction to the outside where it is then discharged. If this reaction space is located in the same reactor as the isothermal reaction space, it is usually connected in a suitable way to the reactor outlet.

The hydrogenation of the aromatic nitro compounds as per step A) of the process of the invention is preferably operated continuously.

The present invention is illustrated with the aid of embodiments. They can be combined with one another in any way unless the opposite is explicitly indicated by the context.

In one embodiment of the process of the invention, the hydrogen gas is circulated through the reactor in step B1). It is possible for further gases to be circulated together with the hydrogen gas. The incondensable gases present in the crude reaction product are then recirculated to the reaction. These gases are essentially inert gases formed during the hydrogenation of unreacted hydrogen and inert gases which have optionally been added or formed by secondary reactions. It is also possible for part of the circulating gas to be branched off, for example when this is desirable in order to keep the concentration of further gaseous components of the circulating gas constant. An example is ammonia formed over the catalyst by deamination reactions.

To achieve circulation of at least the hydrogen gas, the product stream leaving the reactor is cooled to such an extent that the condensable constituents are condensed very completely. Since cooling is subject to limits because of economical boundary conditions, it cannot be ruled out that small amounts of condensable constituents remain in the gas phase. These are then usually conveyed together with the hydrogen via a compressor back into the reactor, so that a hydrogen circuit is ultimately established.

In a further embodiment of the process of the invention, the amount of aromatic nitro compounds and hydrogen is in each case reduced to from ≥1% by mass to ≤40% by mass of the amount previously introduced in step A) before step B). The amount is preferably reduced in each case to from ≥2% by mass to ≤20% by mass, more preferably to in each case from ≥5% by mass to ≤15% by mass. Reducing the amount of aromatic nitro compounds and hydrogen before their introduction is completely stopped avoids relatively large temperature jumps in the reactor and thus stress on the material. Otherwise, the heat of reaction would suddenly be absent.

Furthermore, the amount of hydrogen supplied here during shutting off the introduction of nitroaromatics should be sufficient to reliably react residues of nitroaromatics to completion but also not be too large since the entire hydrogen which has been introduced but not reacted would (provided that the pressure in the plant is constant) be disposed of as purge.

In a further embodiment of the process of the invention, the reactor is filled with an inert gas after step B). A suitable inert gas is, in particular, nitrogen. The filling with inert gas enables the reaction plant to be prepared for regeneration of the hydrogenation catalyst.

As regards the mode of operation of the reactor, preference is given to reaction conditions as described in EP 0 944 578 A2 (isothermal mode of operation) and in EP 0 696 574 B1, EP 0 696 573 B1, EP 1 882 681 A1 (adiabatic mode of operation). It is particularly suitable for the shutdown of the hydrogenation according to the invention when the catalysts as described in U.S. Pat. No. 3,684,740 are regenerated.

In a further embodiment of the process of the invention, step A) is carried out isothermally. This mode of operation has the advantage of a low thermal (change) stress on the reactor material compared to the adiabatic mode of operation.

In a further embodiment of the process of the invention, the molar ratio of hydrogen to nitro groups of the aromatic nitro compounds in step A) is from ≥3:1 to ≤6:1. The lower the excess of hydrogen in the hydrogenation process, the greater the advantages of the process of the invention since the adverse effects occur more frequently and/or to a greater extent.

In a further embodiment of the process of the invention, the predetermined time in step B2) is from ≥10 minutes to ≤600 minutes. The time is more preferably from ≥30 minutes to ≤150 minutes. These times represent a good compromise between the requirement that all nitroaromatics residues should be reacted reliably to completion and, in addition, the plant should be regenerated and brought back to production operation as quickly as possible.

In a further embodiment of the process of the invention, the predetermined concentration of aromatic nitro compounds in the gas stream entering the reactor in step B2 is less than 1000 ppm, preferably less than 100 ppm (ppm by mass). The determination of the concentration can, for example, be carried out by means of previously calibrated on-line gas chromatography.

In a further embodiment of the process of the invention, aromatic nitro compounds having the general formula (I):

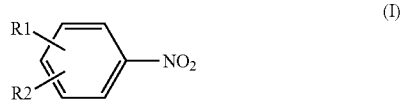

(I)

where $R^1$ and $R^2$ are each, independently of one another, hydrogen, methyl or ethyl and $R^2$ can also be $NO_2$, are used in step A). Preferred aromatic amines are nitrobenzene and dinitrotoluene, so that the hydrogenation thereof gives aniline or toluenediamine.

In a further embodiment of the process of the invention, the catalyst is arranged in a fixed catalyst bed in the reactor. Apart from the abovementioned processes using stationary catalyst beds, processes using fluidized catalyst beds have also been described, e.g. in DE 1114820 B, DE 1133394 B or WO 2008/034770 A1. As an alternative, the catalyst can also be present in a fluidized bed.

The invention is illustrated with the aid of the following examples, without being restricted thereto.

Example 1

Comparative Example, Isothermal

Shutdown of the hydrogenation of nitrobenzene in a plant at the end of a reaction cycle, by shutting off the introduction of hydrogen and the introduction of nitrobenzene at the same time. Consequence: occurrence of an undesirable reduced pressure in the reaction space. In a shell-and-tube reactor thermostatted by means of a Marlotherm® circuit for the hydrogenation of nitrobenzene, nitrobenzene and hydrogen were reacted in a molar ratio of 1:6. A supported noble metal catalyst as described in DE-A 2849002, example 1, served as catalyst and was introduced as a bed into the tubes of the reactor. The excess hydrogen was separated off in the condensation of the reaction products, recovered and reused in the reaction (circulating gas hydrogen).

The condensed reaction products were removed from the reaction system and passed to a work-up. Consumed hydrogen was replaced by fresh hydrogen. A compressor served to circulate the recovered hydrogen. It drew in the hydrogen from the condensers and conveyed it back into the nitrobenzene vaporization. In order to prevent inert components from accumulating in the circulating gas, a side stream was branched off as purge. This was effected via a regulating valve (a dip would be possible as an alternative) which also served as pressure regulator for the reaction system.

To stop the reaction, the introduction of nitrobenzene and fresh hydrogen was interrupted simultaneously. The plant pressure was measured on the suction side of the compressor and monitored. The circulating gas compressors remained in operation during the entire shutdown operation. The plant could then be prepared for subsequent regeneration and renewed start-up by making inert by means of nitrogen. The measured pressures are shown in the table below, it can be seen that a subatmospheric pressure is established in the reactor over the course of time after interruption of the starting material supply.

|  | Point in time: | | | |
| --- | --- | --- | --- | --- |
|  | During the reaction | Interruption of the starting material supply | 5 min after interruption of the starting material supply | 30 min after interruption of the starting material supply |
| Pressure on the suction side of the compressor: | 1.1 bar (a) | 1.1 bar (a) | 1.05 bar (a) | 0.95 bar (a) |

Example 2

Example According to the Invention, Isothermal

In a process as per example 1, the supply of starting materials (nitrobenzene and hydrogen) was firstly reduced to 10% of the nominal load for shutdown of the hydrogenation of nitrobenzene at the end of a reaction cycle.

Proceeding from this state, the introduction of nitrobenzene was interrupted completely while maintaining all other running parameters. The introduction of hydrogen remained in operation for one hour after interruption of the introduction of nitrobenzene and was then likewise interrupted completely. The circulating gas compressors remained in operation during the entire shutdown operation. 30 minutes after interruption of the introduction of hydrogen, le pressure in the plant was checked again before the plant was prepared for subsequent regeneration and renewed start-up by making inert by means of nitrogen.

The measured pressures are shown in the table below. The pressure in the reactor remained stable after interruption of the starting material supply.

| Point in time: | | | | |
|---|---|---|---|---|
| | During the reaction | Interruption of the nitro-benzene supply | 30 min after interruption of the nitrobenzene supply | 90 min after interruption of the nitrobenzene supply (30 min after interruption of the H$_2$ supply) |
| Pressure on the suction side of the compressor: | 1.1 bar (a) | 1.1 bar (a) | 1.1 bar (a) | 1.09 bar (a) |

What is claimed is:

1. A process for preparing aromatic amines by hydrogenation of aromatic nitro compounds, which comprises:
   A) introducing aromatic nitro compounds and hydrogen into a reactor and contacting with a hydrogenation catalyst;
   B) stopping the introduction of aromatic nitro compounds and hydrogen into said reactor;
   characterized in that step B) is carried out by
   B1) firstly stopping the introduction of aromatic nitro compounds into said reactor so that aromatic nitro compounds present in said reactor and/or in plant parts fluidically connected upstream to said reactor react with said hydrogen which continues to be fed into said reactor, and
   B2) subsequently stopping the introduction of hydrogen after a predetermined time and/or after the concentration of aromatic nitro compounds in the gas stream entering the reactor falls below a predetermined value.

2. The process as claimed in claim 1, wherein said hydrogen gas is circulated through said reactor in step B1).

3. The process as claimed in claim 1, wherein the amount of aromatic nitro compounds and hydrogen is reduced in each case to from ≥1% by mass to ≤40% by mass of the amount introduced previously in step A) before step B).

4. The process as claimed in claim 1, wherein said reactor is filled with an inert gas after step B).

5. The process as claimed in claim 1, wherein step A) is carried out isothermally.

6. The process as claimed in claim 1, wherein the molar ratio of hydrogen to nitro groups of said aromatic nitro compounds in step A) is from ≥3:1 to ≤6:1.

7. The process as claimed in claim 1, wherein said predetermined time in step B2) is ≥1 hour.

8. The process as claimed in claim 1, wherein the predetermined concentration of aromatic nitro compounds in said gas stream entering said reactor in step B2) is less than 1000 ppm.

9. The process as claimed in claim 1, wherein aromatic nitro compounds having the general formula (I):

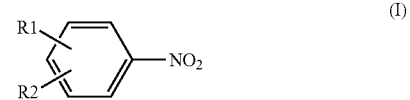

in which:
R1 and R2 are each, independently of one another, hydrogen, methyl or ethyl, with the proviso that R2 can also be NO$_2$, are used in step A).

10. The process as claimed in claim 1, wherein said catalyst is arranged in a fixed catalyst bed in said reactor.

* * * * *